United States Patent [19]
Duce et al.

[11] Patent Number: 5,490,412
[45] Date of Patent: Feb. 13, 1996

[54] EXHAUST SENSOR WITH REMOVABLE ELECTRICAL CONNECTOR

[75] Inventors: Richard W. Duce, Flushing; David B. Quinn, Grand Blanc; Kathryn M. McCauley, Durand, all of Mich.

[73] Assignee: General Motors Corporation, Detroit, Mich.

[21] Appl. No.: 59,399

[22] Filed: May 11, 1993

[51] Int. Cl.⁶ .......................... G01N 30/02; G01M 19/00
[52] U.S. Cl. ......................................... 73/23.31; 73/118.1
[58] Field of Search ................... 73/23.31, 23.32, 73/118.1, 116; 439/350, 353, 271, 320, 321, 322

[56] References Cited

U.S. PATENT DOCUMENTS

| | | | |
|---|---|---|---|
| 3,824,523 | 7/1974 | McGhee | 439/350 |
| 3,909,385 | 9/1975 | Spielberg et al. | 204/195 S |
| 4,151,503 | 4/1979 | Cermak et al. | 73/23.31 |
| 4,309,897 | 1/1982 | Springer et al. | 73/23.31 |
| 4,389,081 | 6/1983 | Gallusser et al. | 439/320 |
| 4,443,052 | 4/1984 | Eaby et al. | 439/322 |
| 4,449,776 | 5/1984 | Carmo et al. | 439/350 |
| 4,469,626 | 9/1984 | Tuohig et al. | 252/514 |
| 4,521,066 | 6/1985 | Kempe et al. | 439/320 |
| 5,031,445 | 7/1991 | Kato | 73/23.31 |
| 5,046,964 | 9/1991 | Welsh et al. | 439/321 |
| 5,181,860 | 1/1993 | Honma et al. | 439/321 |
| 5,329,806 | 7/1994 | McClanahan et al. | 73/31.05 |

FOREIGN PATENT DOCUMENTS

| | | |
|---|---|---|
| 0364315 | 9/1989 | European Pat. Off. . |
| 0398625 | 5/1990 | European Pat. Off. . |
| 2855012 | 6/1980 | Germany . |
| 2105050 | 10/1988 | Japan . |
| 3180748 | 8/1991 | Japan . |

OTHER PUBLICATIONS

European Search Report Application No. EP 94 20 1058 corresponding to U.S. Ser. No. 08/059,399 dated 2 Sep. 1994.
Annex to the European Search Report Application No. EP 94 20 1058.
European Search Report Application No. EP 94 20 1060 corres. to U.S. Pat. No. 5,329,806 dated 2 Sep. 1994.
Annex to European Search Report Application No. EP 94 20 1060.

*Primary Examiner*—Richard E. Chilcot, Jr.
*Assistant Examiner*—William L. Oen
*Attorney, Agent, or Firm*—Cary W. Brooks

[57] ABSTRACT

Disclosed is an exhaust oxygen sensor including a component requiring electricity to operate such as a heater or oxygen electrode. The first electrical terminal is provided in electrical contact with the component and wherein the electrical terminal has at least one male prong. The second electrical terminal in electrical contact with a wire for delivering electrical power from an external source is also provided. The second electrical terminal has at least one female connector or receptacle. The male prong and the female connector are constructed and arranged so at least one of the first and second electrical terminals is removable with respect to the other terminal. The sensor may include a threaded nut slidably received over a tubular housing, constructed and arranged to be threaded onto a threaded exhaust manifold boss without rotating the housing.

6 Claims, 6 Drawing Sheets

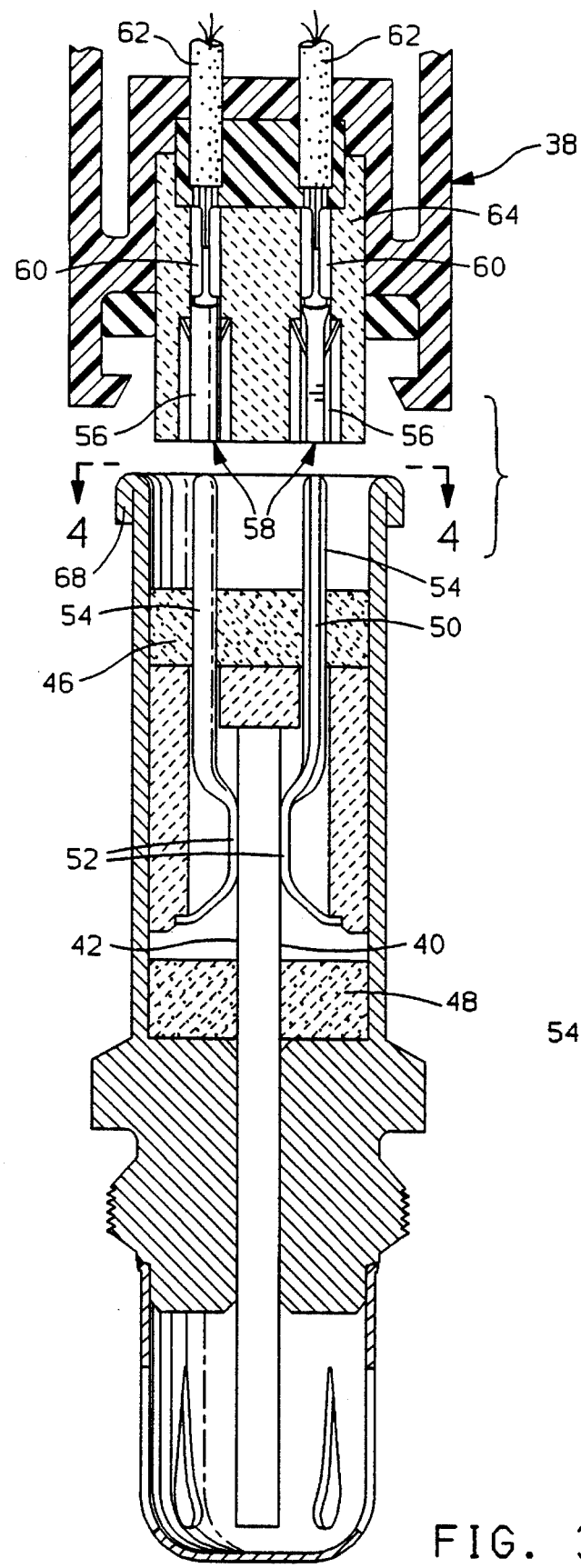
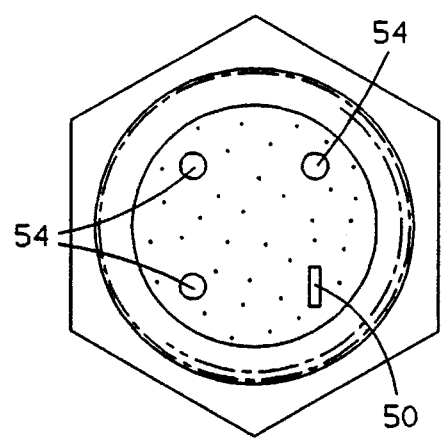
FIG. 3
FIG. 4

5,490,412

EXHAUST SENSOR WITH REMOVABLE ELECTRICAL CONNECTOR

FIELD OF THE INVENTION

This invention relates to gas sensors, and more particularly to automotive exhaust oxygen sensors having removable electrical connectors.

BACKGROUND OF THE INVENTION

Automotive exhaust oxygen sensors have elements such as electrodes or heaters, which require electricity. FIG. 1 illustrates a prior oxygen sensor 10 in which electricity or power is provided to a sensing element or a heater 12 through permanent crimped contacts. The contacts have a terminal pad 14 permanently connected or soldered to the body of the sensor or to an associated terminal pad on the heater. The contact at the other end includes a crimped portion 16 which surrounds and contacts a wire 18 supplying electricity or power to the component. The wire then extends through the housing body 20 and is connected to an external power source. Assembling such a sensor requires the sensor body to be permanently attached to a link of cable with an interface connector. That assembly process is extremely difficult and undesirable. Many added steps and special tools are required to connect a sensor with an attached harness to a manifold boss. The attached harness assemblies can tangle and nest together making it difficult to pull out one sensor from a bulk load. Two hands are required to screw the sensor into the manifold to prevent the wires from tangling. A special tool designed to fit around the harness assembly and wires is required to tighten the sensor into the boss. Further, the wires must be secured to the engine prior to installation of the sensor into the vehicle so that damage to the wires and the vehicle interface connector is prevented.

The present invention overcomes the deficiencies of these prior oxygen sensors.

SUMMARY OF THE INVENTION

The invention relates to an automotive exhaust oxygen sensor including a component requiring electricity to operate, such as a heater or electrode. A first electrical terminal having at least one male prong is provided in electrical contact with the component. A second electrical terminal is provided in contact with a wire for delivering electrical power from an external source. The second electrical terminal has at least one female receptacle for receiving a corresponding male prong of the first electrical terminal. The male prong and the female receptacle are constructed and arranged so at least one of the first and second electrical terminals is removable with respect to the other terminal. The removable electrical connector greatly improves the ease of assembly and repair of the oxygen sensor.

These and other objects, features and advantages and embodiments will be apparent from the following brief description of the drawings, detailed description, appended claims and drawings.

BRIEF DESCRIPTION OF THE DRAWINGS

FIG. 3 is a sectional exploded view taken along line 3—3 of FIG. 2;

FIG. 4 is a sectional view taken along line 4—4 of FIG. 3;

DETAILED DESCRIPTION OF THE INVENTION

Figure 1:
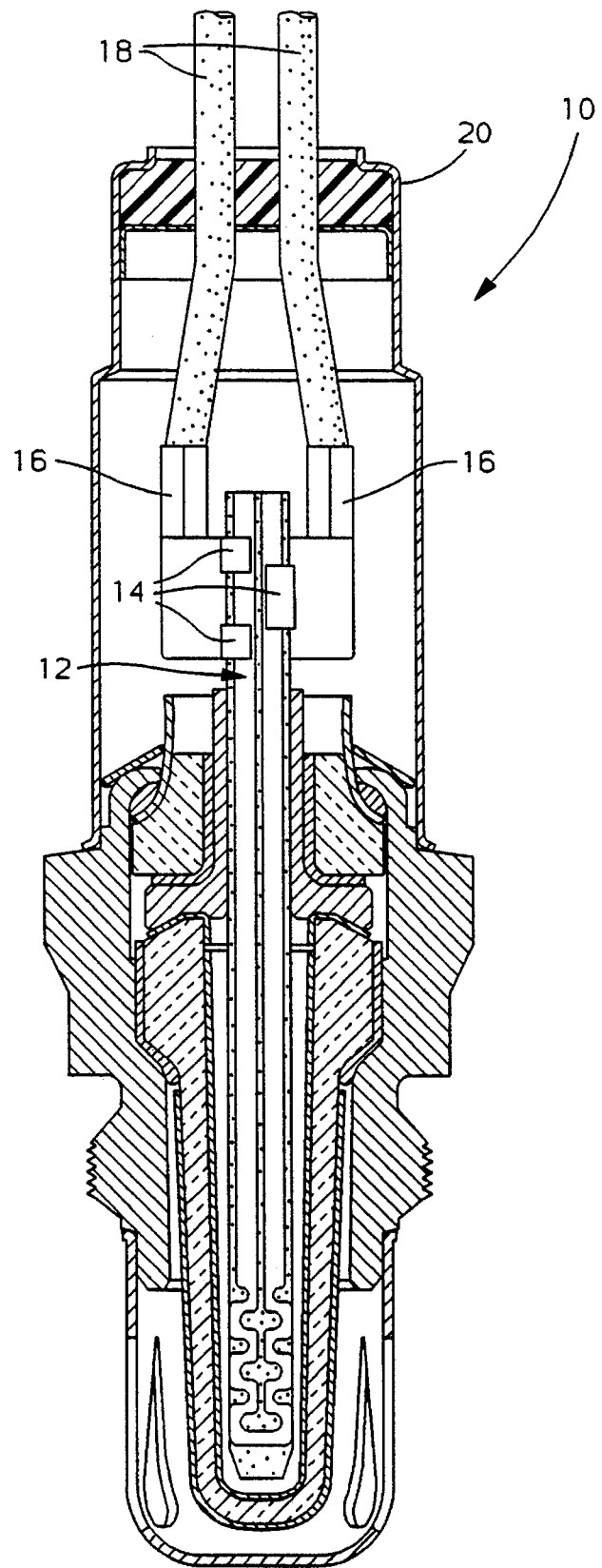
FIG. 1 illustrates a prior exhaust oxygen sensor.

Exhaust oxygen sensors are used in automobiles to determine the concentration of oxygen in the exhaust gas of an engine. By measuring the concentration of the oxygen content in the exhaust gas, various parameters can be adjusted to operate the engine for improved performance and limited environmental emissions. In general, exhaust oxygen sensors include a pair of electrodes positioned on opposite sides of an oxygen permeable material such as an electrolyte body. As electricity is supplied to the electrodes, gas migrates through the oxygen permeable material. The rate of oxygen transfer through the permeable material is measured to determine the concentration of the oxygen in the exhaust gas. Often a heater is provided so that both reference oxygen and exhaust oxygen is maintained at predetermined temperature. The electrode and the heater require electrical power to operate. The prior exhaust oxygen sensors included terminals permanently soldered to the sensor body or a terminal pad on a heater as shown in FIG. 1. Another portion of the terminal was crimped around a wire which was connected to an external power source. The disadvantages of such systems are outlined above.

Figure 2:
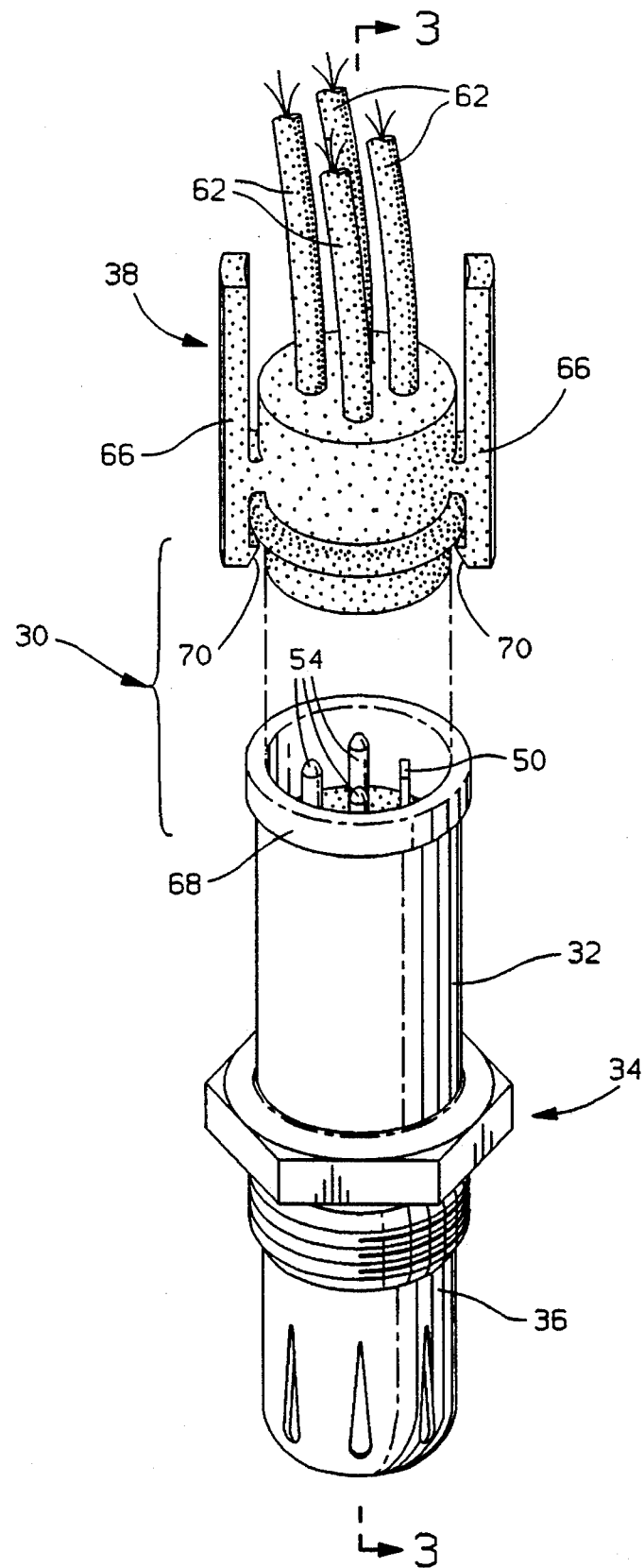
FIG. 2 illustrates a gas sensor according to the present invention.

In contrast, FIGS. 2, 3 and 4 illustrate an exhaust oxygen sensor 30 according to the present invention. The oxygen sensor includes an upper shield 32, a body 34, a lower shield 36 and a cap 38 all connected together to form the oxygen sensor housing. The upper and lower shields 32, 36 are made from a tubular-shaped stainless steel material about 0.5 mm thick. The body is made from a stainless material about 2.5 mm thick at the smallest cross section. The body has a threaded portion 37 on its outer surface near a lower end which may be threaded into a manifold boss. A heater element 40 and an oxygen sensing element 42 are received in the housing and held in position by cylindrical ceramic connector 44 and upper and lower glass seals 46, 48 respectively, which extend from the shell to the flat plate oxygen sensor element or terminals 50. The terminals 50 are provided for separate connection to first and second leads of the heater; to the electrode of the oxygen sensor element; and to a ground. The terminals may include a terminal pad 52 welded to the heater or the oxygen sensor element. Male prongs 54 extend upward from each terminal pad. The male prongs may be held in place by upper glass seal 46 or a spacer-orienting alumina material which acts as a terminal holder. A suitable glass seal for the holder includes fused alumina borosilicate glass. A second terminal is provided in the cap 38 with a corresponding female connector for each male prong. The female connector includes a metal portion 56 defining a cavity 58 for receiving at least a portion of the male prong. The female connector also includes a crimped portion 60 which is crimped around a wire 62 which extends out of the oxygen sensor housing to an external power source. The female connectors may be held in position by a plug 64 or seal which may be inserted into the oxygen sensor cap. The male prong and the female connectors may be made of any electrical conducting material, for example, gold-plated stainless steel.

The orientation of the male prong and the female receptacle for each electrical terminal may be varied, and each terminal may have at least one male prong and female receptacle. The male prongs and female receptacles may be arranged on each electrical terminal to insure that the first and second oxygen terminals are always connected and assembled properly. As shown in FIG. 4, the male prong may have a variety of shapes including substantially cylindrical or substantially rectangular in cross-sectional. The corresponding female receptacle is designed to define a cavity for receiving the particular shape of the corresponding male prong on the opposite terminal. The male prong and the female receptacle are constructed and arranged so that at least one of the first and second electrical terminals are removable with respect to the other terminal.

As shown in FIGS. 2 and 3, the cap may include a first resilient lock 66 for releasably locking onto a ridge 68 formed on an upper portion of the body of the sensor. The first resilient lock may be an inwardly extending lip 70 or a resilient finger at the lower edge of the cap. The cap may be pushed against the body so that the first terminal in the oxygen sensor body and second terminal in the cap make electrical connection with the male prongs being received in female receptacles. The resilient first lock of the cap is pressure fitted around the ridge of the body to close the oxygen sensor. Thereafter, the cap may be permanently secured to the shell by welding, cement or other suitable means.

Figure 5:
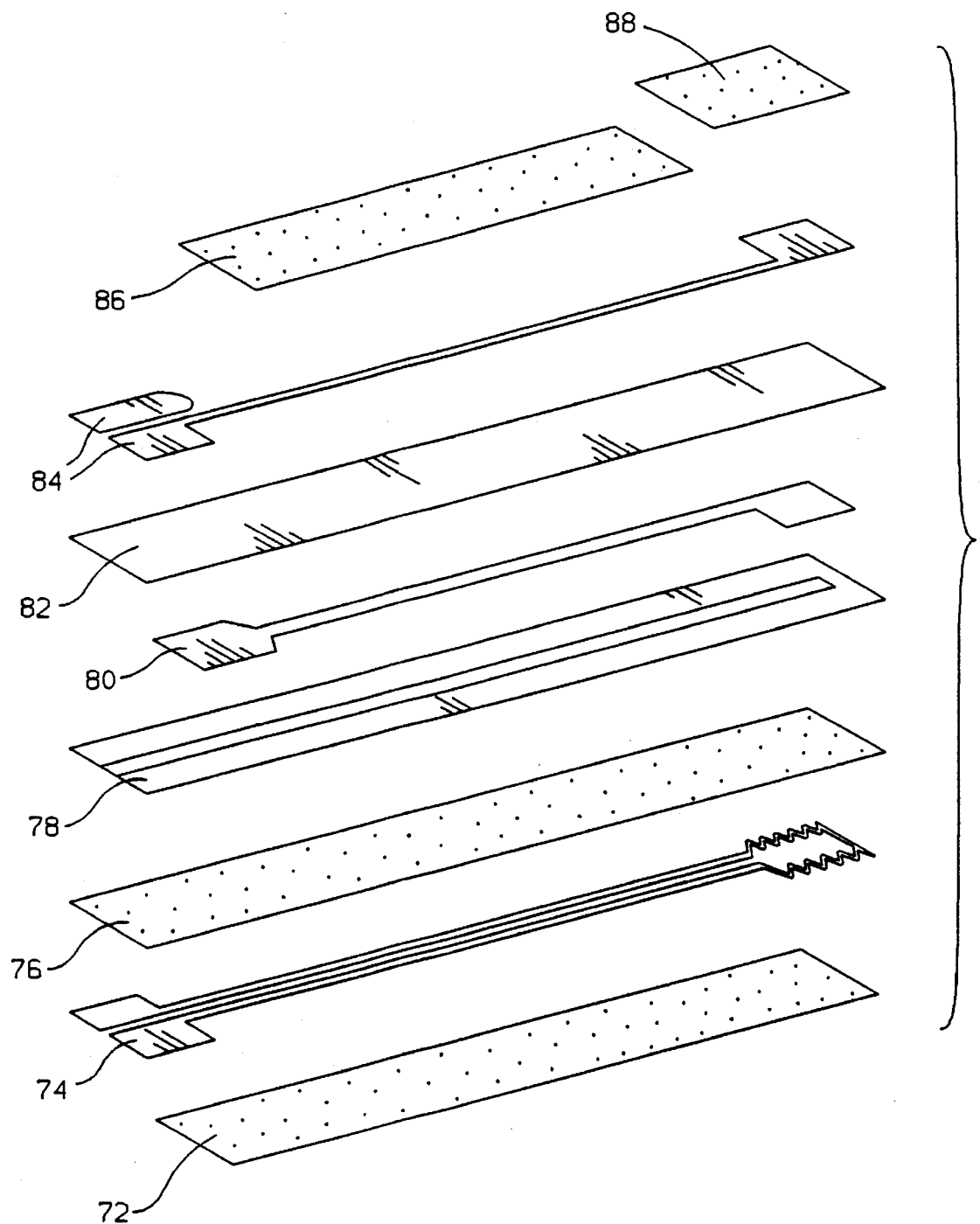
FIG. 5 is an exploded view of a flat plate oxygen sensor useable in the present invention.

A variety of flat plate oxygen sensors are known to those skilled in the art which are suitable for use in the present invention. FIG. 5 illustrates such a flat plate oxygen sensor which includes a series of laminated structures overlaying each other including, for example, a heater protective coat 72, a platinum heater 74, a heater insulating layer 76, a heater substrate 78, a platinum inner electrode 80, a zirconium electrode substrate (electrolyte body) 82, a platinum outer electrode 84, an electrode lead productive coat 86, and an electrode protective coat 88. The male prongs and female prongs described herein are arranged to make electrical connection to the platinum heater, and the inner and outer platinum electrodes.

Figure 6:
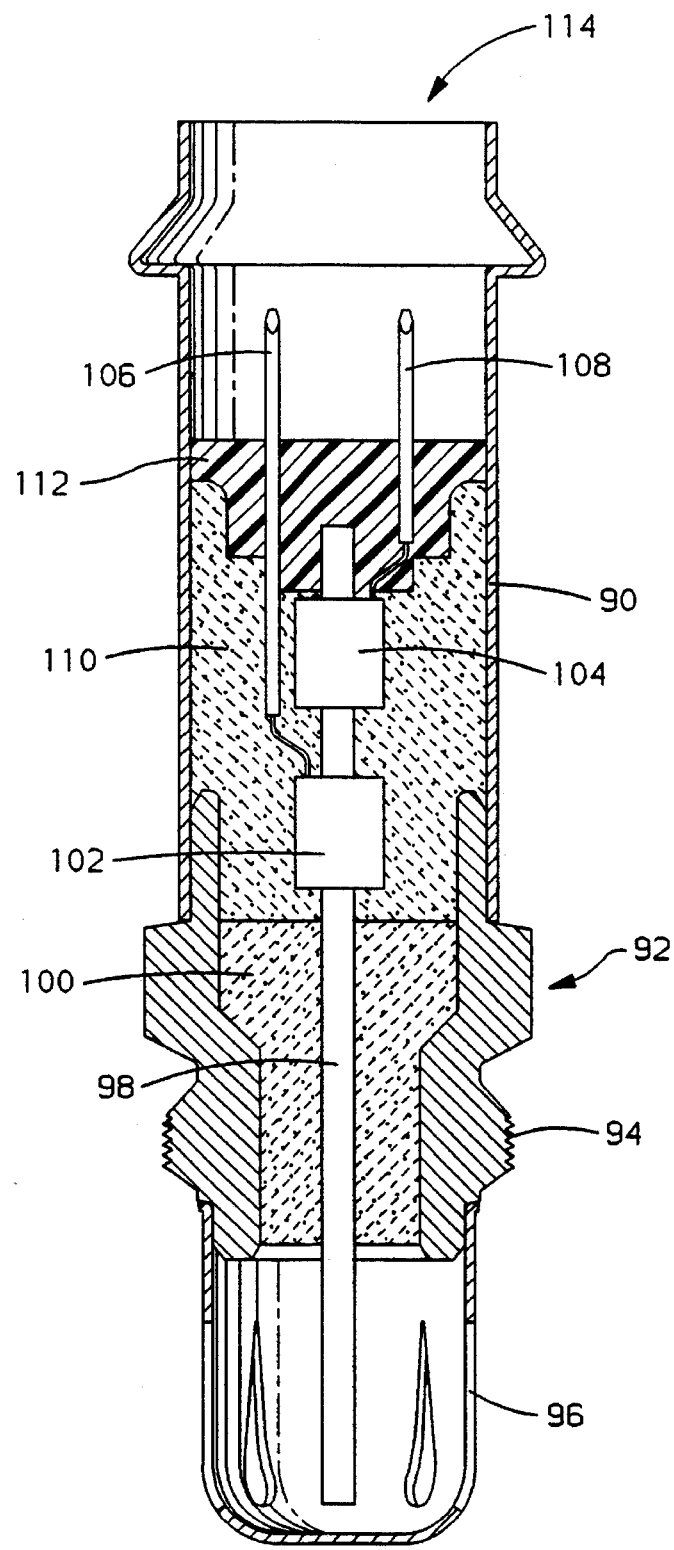
FIG. 6 is a sectional view of another embodiment of a gas sensor according to the present invention.

FIG. 6 illustrates another embodiment of the present invention. This embodiment includes an upper tubularly shaped shield 90, a cylindrical metal body 92 having a threaded portion 94 near a lower end, and a closed end tubularly shaped lower shield 96 connected together to form an oxygen sensor housing. A flat plate oxygen sensing element with a heater 98 is received in the housing and held in position by cement 100 extending from the walls metal body to the flat plate sensor. The flat plate sensing element has electrical terminals 102, 104 connected thereto near an upper end and male prongs 106, 108 extend upwardly therefrom. A glass seal 110 extends from walls of the upper shield to surround an upper portion of the flat plate sensing element, the electrical terminals. The male prongs are held in position by a spacer orienting alumina ceramic 112 extending from the walls of the upper shield to the prongs. A space 114 is provided in the upper portion of the upper shield for receiving a rubber stopper carrying electrical terminal having female receptacles for receiving an associated male prong. Wires connect the electrical terminals to an external power source.

Figure 7:
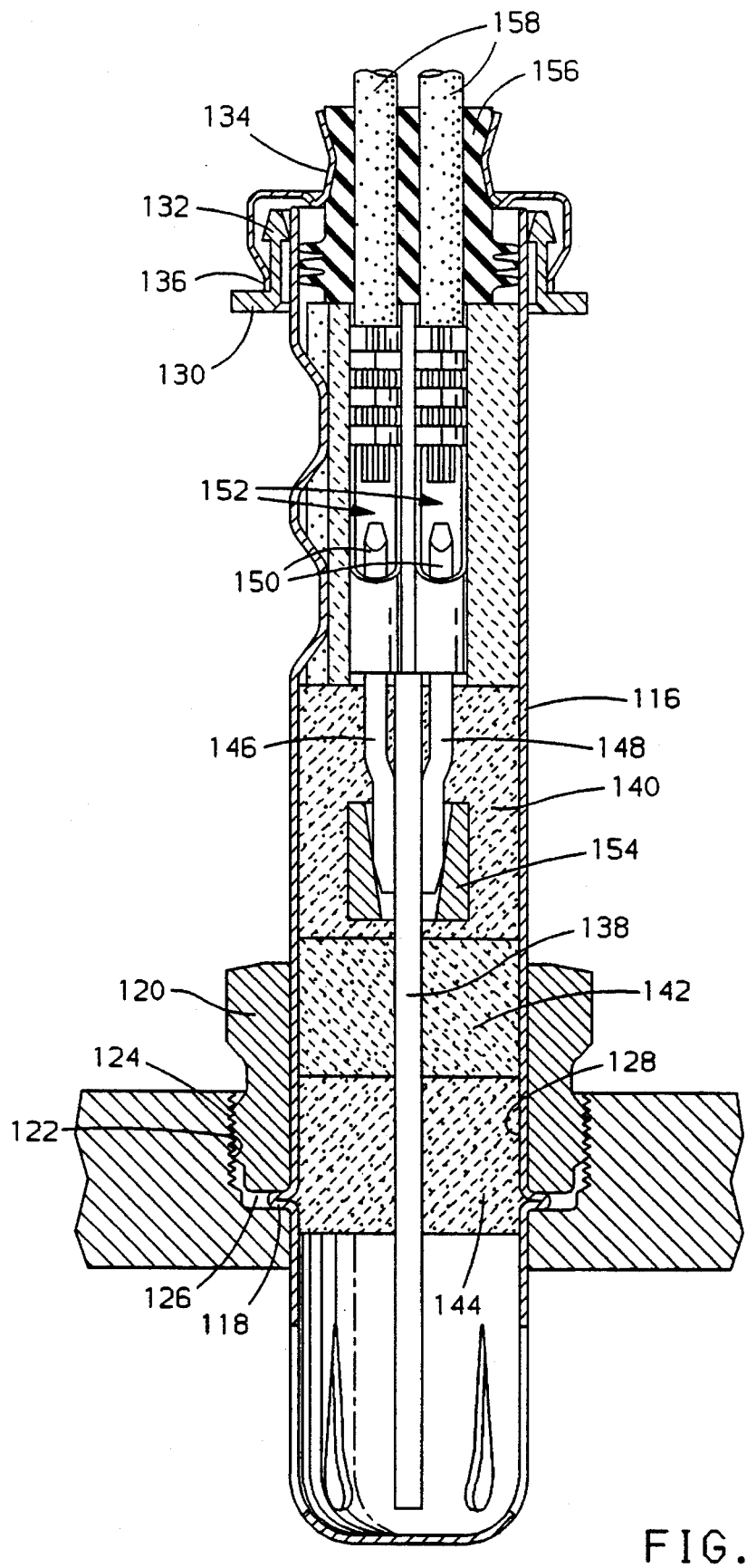
FIG. 7 is a sectional view of another embodiment of a gas sensor according to the present invention with a slidable hex nut.

FIG. 7 illustrates another embodiment of the present invention. This embodiment includes a single piece tubular shell 116 made out of stainless steel material about 0.5 mm thick. The shell has a crimped lip 118 formed near the lower portion of the shell. A ring-shaped hex nut 120 is slipped over the tubular shell for engagement with the crimped lip. The hex nut includes a threaded portion 122 corresponding to a threaded boss 124 in the exhaust system. The crimped lip 118 on the shell prevents the oxygen sensor from being pushed in or pulled out of the boss. The hex nut cooperates with a seat 126 formed in the boss to prevent the oxygen sensor from being pushed too far into the boss. The crimped lip on the shell could be eliminated if the hex nut and shell are designed to provide a frictional fit. The tube could have a slightly larger diameter in a desired area 128 to provide the frictional fit. The nut is threaded into the boss to hold the sensor in place without the need to rotate the shell. This eliminates the need for special tools to assemble and install the sensor.

A barbed ring 130 is slipped over the upper portion of the tubular shell and includes a barb 132 for engaging the shell. A retainer 134, made out of stainless steel material about 0.5 mm thick, is slipped over the upper portion of the shell and the barbed ring. The retainer has an inwardly biased leg 136 or finger for engaging the barbed ring and sealing the upper portion of the oxygen sensor. A flat plate oxygen sensor 138 is housed in the shell and is held in position by a first cement composition 140 surrounding an upper portion of the flat plate oxygen sensor; a glass seal 142 surrounding the middle portion of the oxygen sensor; and a second cement composition 144 surrounding a lower portion of the flat plate oxygen sensor. A suitable cement composition includes calcia alumina (calcium aluminate, 3 $CaO.Al_2O_3$) and is available from Aremco Company under the trade name Ceramcast 575™. A suitable glass seal composition includes glass frit and is available from Ferro Company under the trade name 2876™. The first and second cement composition firmly holds the flat plate oxygen sensor in the shell and the glass seal allows for thermal expansion of the flat plate oxygen sensor. First and second terminals 146, 148 are used to make electrical connection to the heater and flat plate electrodes by way of male prongs 150 and female receptacles 152 as described above. Two electrical connections are made to the heater portion of the flat plate oxygen sensor as described above. One electrical connection is made to the inner electrode of the flat plate sensor. A fourth terminal is connected to the outer electrode to provide an isolated ground back to an electronic control module. A wedged ring 154 may be positioned around the electrical connections to the flat plate oxygen sensor to create electrical contact with the element and hold the terminals in place until the braze is cured. A teflon seal 156 is provided within the retainer and has holes formed therein to accommodate the electrical cables 158 associated with the electrical connector. The retainer barbed ring and teflon seal make the oxygen sensor waterproof.

The embodiments of the invention in which an exclusive property or privilege is claimed are defined as follows:

1. An automotive exhaust sensor comprising:

a component requiring electrical power to operate;

a first electrical terminal in electrical contact with said component, said first electrical terminal having a male prong;

a second electrical terminal in electrical contact with a plurality of wires for delivering electrical power from an external source, said second electrical terminal having a female receptacle;

said male prong and female receptacle being constructed and arranged so that at least one of said terminals is selectively removable with respect to the other; and further comprising an upper shield, a shell and a lower shield, and said component being carried by said shell; said first terminal being received in said upper shield and said second terminal being carried by said shell; said upper shield having a resilient locking finger at a lower end and said shell having a ridge at an upper end so that the resilient locking finger of the upper shield is pressure fitted around the ridge of the shell, and so that the first and second terminals are in electrical contact, and said shell having a threaded portion.

2. An automotive exhaust sensor as set forth in claim 1 further comprising a holder for permanently holding said male prong in a predetermined position.

3. An automotive exhaust sensor as set forth in claim 2 wherein said holder is a glass seal surrounding a portion of said male prong.

4. An automotive exhaust sensor as set forth in claim 3 wherein said glass seal comprises fused alumina borosilicate glass.

5. An automotive exhaust sensor as set forth in claim 1 wherein said female receptacle further comprises a first portion secured to said wire.

6. An automotive exhaust oxygen sensor comprising:

a tubular shaped shell having a threaded portion in an outer surface and having an oxygen sensor element carried therein and a first electrical terminal including male prongs connected to said oxygen sensing element;

a cap having a second electrical terminal received therein including female receptacles for engagement with said male prongs;

said cap including a first resilient locking member for releasably locking onto a ridge formed on the upper portion of the tubular shell so that said first and second terminals make electrical contact to the oxygen sensing element and so that said first and second terminals are removable with respect to each other.

\* \* \* \* \*